US006176879B1

(12) United States Patent
Reischl et al.

(10) Patent No.: US 6,176,879 B1
(45) Date of Patent: Jan. 23, 2001

(54) MEDICAL IMPLANT

(75) Inventors: Gabriele E. Reischl, München; Rolf Martin Lehner, Esslingen; Dieter Müller, Meitingen; Hans Leysieffer, Taufkirchen, all of (DE)

(73) Assignee: Implex Aktienegesellschaft Hearing Technology, Ismaning (DE)

( * ) Notice: Under 35 U.S.C. 154(b), the term of this patent shall be extended for 0 days.

(21) Appl. No.: 09/209,275

(22) Filed: Dec. 11, 1998

(30) Foreign Application Priority Data

Jul. 2, 1998 (DE) .............................................. 198 29 637

(51) Int. Cl.[7] .............................................. A61F 2/02
(52) U.S. Cl. .............................................. 623/11.11; 623/17.19
(58) Field of Search .............................................. 623/10, 24, 11.11, 623/17.19; 321/322, 312, 23.1; 381/69.2; 607/36

(56) References Cited

U.S. PATENT DOCUMENTS 2,495,476 * 1/1950 Posen .
3,798,390 * 3/1974 Gage .............................................. 607/36
4,419,995 12/1983 Hochmair et al. .
4,991,582 2/1991 Byers et al. .
5,271,397 * 12/1993 Seligman .............................................. 623/10
5,279,292 1/1994 Baumann et al. .
5,411,467 5/1995 Hortmann et al. .
5,645,586 * 7/1997 Meltzer .............................................. 607/36
5,724,431 * 3/1998 Rieter .............................................. 381/69.2
5,792,208 * 8/1998 Gray .............................................. 607/36
5,814,095 9/1998 Müller et al. .
5,895,414 * 4/1999 Sanchez-Zambrano .............................................. 607/36
5,984,859 * 11/1999 Lesinski .............................................. 623/10
6,001,129 * 12/1999 Bushek .............................................. 623/10

FOREIGN PATENT DOCUMENTS 39 18 329 12/1990 (DE) .
39 40 632 12/1990 (DE) .
WO 92/20402 * 11/1992 (WO) .............................................. 607/36
WO 97/44987 11/1997 (WO) .

* cited by examiner

*Primary Examiner*—Michael J. Milano
(74) *Attorney, Agent, or Firm*—Nixon Peabody, LLP; David S. Safran

(57) ABSTRACT

Medical implant which is suitable for implantation in an artificial bone bed surgically made on the outer surface of the mastoid region of the skull, having a hermetically sealed housing in which electronic components and other components or modules are accommodated. The implant housing is provided with at least on bend in at least one plane which is dimensioned such that in a plane perpendicular to the direction of the bend, a tangential line extending from a bottom portion of one housing end forms an angle, preferably an angle between 5° to 25°, with a tangent extending from a bottom portion of another housing end.

25 Claims, 2 Drawing Sheets

MEDICAL IMPLANT

BACKGROUND OF THE INVENTION

1. Field of the Invention

The invention relates to a medical implant which is suitable for implantation in an artificial bone bed on the mastoid region of the skull having a hermetically sealed housing in which an electronic component and optionally, other components or modules are accommodated.

2. Description of the Related Art

Implants of this general type are known in the art as exemplified by U.S. Pat. No. 5,411,467 to Hortmann et al. and by the published German patent application No. DE 39 18 329 A1. Such implants are surgically imbedded in the bony area of the skull behind the ear which is known as the mastoid. An artificial bone bed can be created in the mastoid to receive the housing of the implant. The designs of these implant housings are difficult in that there are severe size limitations. One major design limitation lies in the fact that the size of the bone bed must be kept as small as possible. Another limitation lies in the fact that the depth of the bone bed must be kept as shallow as possible. On the other hand, any projection of the housing above the outside edge of the bone bed would result in bulging of the skin above the housing which would not be desirable since one of the goals and benefits of such implants is to make the implants and the aiding devices inconspicuous. Of course, this design difficulty is exacerbated when the medical implant requires a volumetrically large housing. This can arise when the implant's electronics or other components are relatively large and complex such as a power supply unit or components thereof In known implantable cochlea implants such as Nucleus 22 and Nucleus 24 Cochlea Implant System from Firma Cochlear AG, a receiver/stimulator electronic module is accommodated in a titanium housing which includes a silastic jacket. The silastic jacket forms a thin, flexible silastic flap (for example, 2.5 mm thick) which extends away from one side of the titanium housing and holds a receiving antenna coil together with a magnet. During the implantation, only the titanium housing is inserted into the bone bed while the thin flexible flap holding the antenna coil and/or magnet is placed on the outside of the bone bed. This flexible flap is then covered by the skin. The flexible silastic flap however, does not provide a hermetically air-tight sealing of the components enclosed therein. Although flexibility of the flap allows it to conform to the curved shape of the skull, there is a danger of breakage in the connections between the components held in the silastic flap and the components located in the titanium housing. Moreover, because the thickness of the flap is limited so that the skin over the flap does not disruptively bulge, this also severely limits the size of the implant components and the type of components which can be held within the flexible silastic flap.

SUMMARY OF THE INVENTION

A primary object of the present invention is to devise a medical implant with a housing which maximizes the volume available in the housing for holding implant components.

Another object of the present invention is to provide a medical implant with a housing that minimizes any protrusion beyond the artificial bone bed in the mastoid of the skull such that bulges in the skin can also be minimized.

These objects are achieved in the present invention by providing a medical implant suitable for implantation in an artificial bone bed formed on the mastoid region of the skull which includes a hermetically sealed housing in which electronic implant and implant components may be accommodated where the housing includes at least one bend in at least one plane. The bend is dimensioned such that a tangential line extending from a bottom portion of one housing end forms an angle with a tangent extending from the other housing end.

Preferably, the implant housing in accordance with the present invention includes a bend in the middle third region or roughly in the middle half region of the housing. The angle formed by the tangents may be between 5 degrees and 25 degrees. More preferably, the angle formed by the tangents may be between 7 to 15 degrees. An angle of approximately 10 degrees has proven especially favorable. Furthermore, in accordance with another embodiment of the present invention, the implant housing may include multiple bends on a single plane.

In another embodiment of the present invention, the largest dimension of the housing, which is generally the length of the housing, is between 30 mm to 55 mm and more preferably, is between 38 mm to 50 mm. In many applications, the direction of the bend in the housing would run perpendicular to this largest dimension. The smallest dimension of the housing which is generally the thickness of the housing, is preferably between 4 mm to 8 mm.

The housing is also preferably made rigid such as shown in U.S. Pat. No. 4,991,582 to Byers et al. thereby reducing mechanical stresses on the components housed therein and on the electrical connections. In this regard, a portion of the housing can be made from a ceramic. The housing can also include multiple portions such as a ceramic housing portion and a metal housing portion. This housing design would result in a housing which is at least partially transparent to electrical, magnetic and electromagnetic fields. This is important if, for example, the housing is to accommodate an energy and/or data receiving antenna and/or a data transmitting antenna, or an antenna used for receiving and transmitting data as well as for receiving energy, particularly energy used to directly operate the medical implant and/or to recharge a trancutaneously rechargeable power supply unit of the medical implant. But as evident to those skilled in the art, the housing can also be made from a metal depending on the special design and application of the implant and the housing.

In one embodiment of a housing with a ceramic housing portion and a metal housing portion, the bend is advantageously placed in the vicinity of where the ceramic housing portion joins with the metal housing portion. This embodiment is especially adaptable for containing a power supply unit, particularly a trancutaneously rechargeable power supply unit, or at least a component thereof, in one housing portion and an electronic component in the other housing portion.

For example, the present implant housing can be used effectively in totally or partially implantable hearing aid systems, especially in such systems that actively stimulate the inner ear through mechanical or electrical stimulation. These types of hearing aids are known in the art as exemplified in U.S. Pat. No. 5,411,467 to Hortmann et al., U.S. Pat. No. 5,279,292 to Baumann et al. and U.S. Pat. No. 4,419,995 to Hochmair et al. These types of hearing aids are further exemplified in the German patent DE 39 40 632 C1, and the German patent applications, DE 39 18 329 A1, and DE 196 38 159.2 and its related U.S. Pat. No. 5,814,095 commonly assigned to the present applicant.

Although the above discussion focused on the present invention's application in hearing said systems, the invention is in no way limited thereto. The present invention may also be used in the like manner for any other implants. Of course, the above discussed embodiment of the present invention is especially applicable for implantation in the mastoid region of the skull. Other examples of these implants include tinnitus suppression systems, drug pumps and retinal stimulators and others.

The preferred embodiments of the present invention are set forth in detail below together attached drawings.

DETAILED DESCRIPTION OF THE INVENTION

Figure 1:
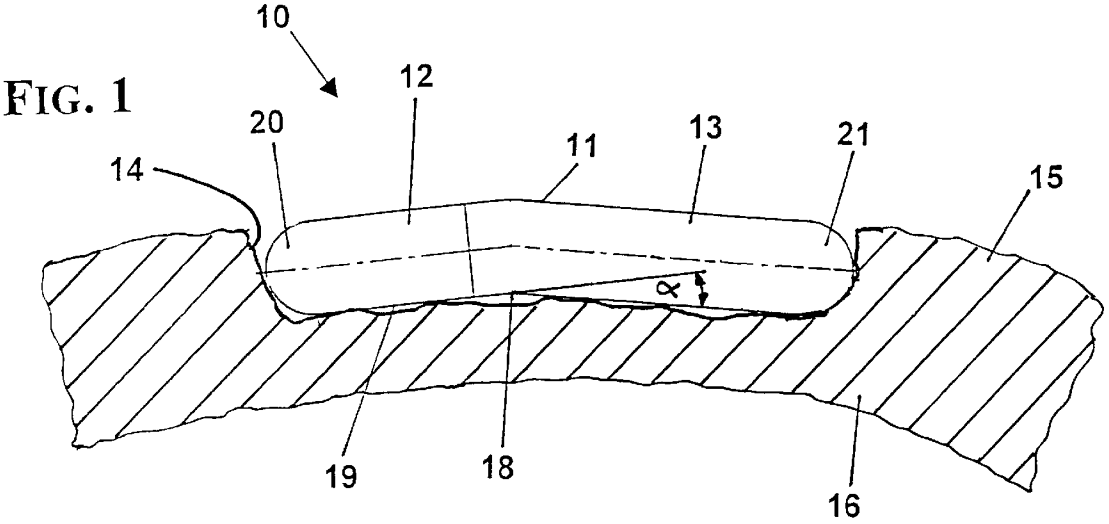
FIG. 1 shows a side view of a medical implant in accordance with the present invention which is fitted into the artificial bone bed in the mastoid region of the skull.

An implant in accordance with one embodiment of the present invention is illustrated in FIG. 1, where an implant 10 is shown as including a housing 11 with a ceramic housing portion 12 and a metal housing portion 13. Housing 11 is inserted into an artificial bone bed 14 surgically made on the outer-side 15 of the skull 16, especially in the mastoid region. The ceramic housing portion 12 of the present invention can hold, for example, a coil 26 adapted to be used as a receiving coil of an energy charging system for recharging an energy storage device of the implant. Such energy storage systems are known in the art as exemplified in U.S. Pat. No. 5,279,292 noted previously and thus, need not be detailed here. Coil 26 additionally may be used for receiving data and/or for transmitting data from and to, respectively, an extracorporal unit as exemplified in U.S. Pat. No. 5,713,939 to Nedungadi et al. It is also possible to provide separate coils for energy transmission and data transmission as exemplified in U.S. Pat. No. 3,942,535 to Schulman. Again, as an example, the metal housing portion 13 can hold an electronic module 24, such as an energy storage device, electrically connected to the receiving coil 26 held in the ceramic housing portion 12. As an example, the electronic module 24 can be a component of an active hearing aid for mechanical or electrical stimulation of the middle ear and the coil 26 can form part of the implantable power supply unit and optionally also can be used for transcutaneous data transmission. These electronic modules may be made in the conventional manner already known in the art as disclosed in the references cited above.

Again, as an example only, FIG. 1 clearly shows housing 11 including a bend 18 in its middle third region that runs continuously across the width of the housing which is perpendicular to the longitudinal direction of the housing. In the present example, the bend 18 is located in the vicinity of the site where the ceramic housing portion 12 joins the metal housing portion 13. The bend 18 is also dimensioned such that a tangential line extending from a bottom portion 19 on one housing end 20 forms an angle $\alpha$ with a tangent extending from the other housing end 21 as shown in FIG. 1. The angle $\alpha$ may be generally in the range from 5° to 25° but preferably, the angle $\alpha$ is approximately 100. The longitudinal dimension of the housing 11 may be in the range from 30 mm to 55 mm, and may have a thickness in the range from 4 mm to 8 mm.

Figure 2:
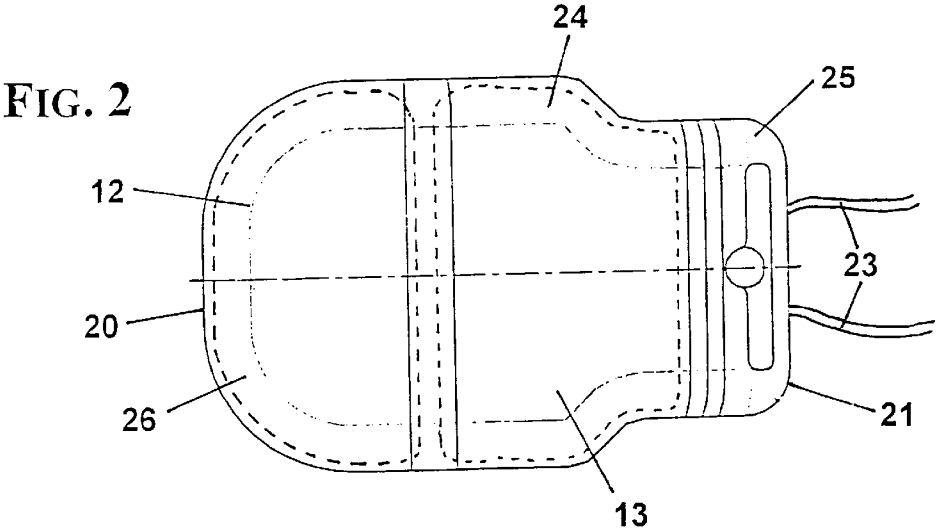
FIG. 2 shows a top plan view of the implant shown in FIG. 1.

As FIG. 2 illustrates in an top plan view of the implant, one or more connecting cables 23 can be routed out from the hermetically sealed housing 11. The connecting cables 23 may also be detachably attached to an electronic module 24 held in the metal housing 13 by utilizing a contact arrangement know in the art and exemplified in U.S. Pat. No. 5,755,743 to Volz et al. This type of contact arrangement may be located in a removable cover 25 of implant 10. FIG. 2 also schematically shows the aforementioned receiving coil 26. The coil 26 may also be used as a sending and/or receiving coil to transfer information from the implant to a receiver outside the body and vice versa.

Figure 3:
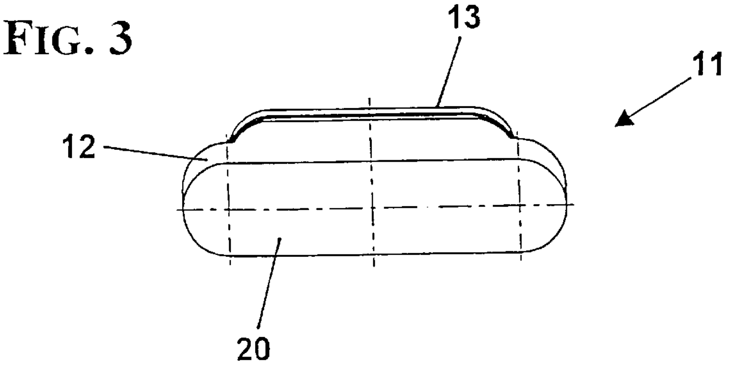
FIG. 3 shows a frontal view of the implant shown in FIG. 1.

FIG. 3 shows a frontal view of the implant shown in FIG. 1 as viewed from the housing end 20 showing the ceramic housing portion 12 and the metal housing portion 13.

Figure 4:
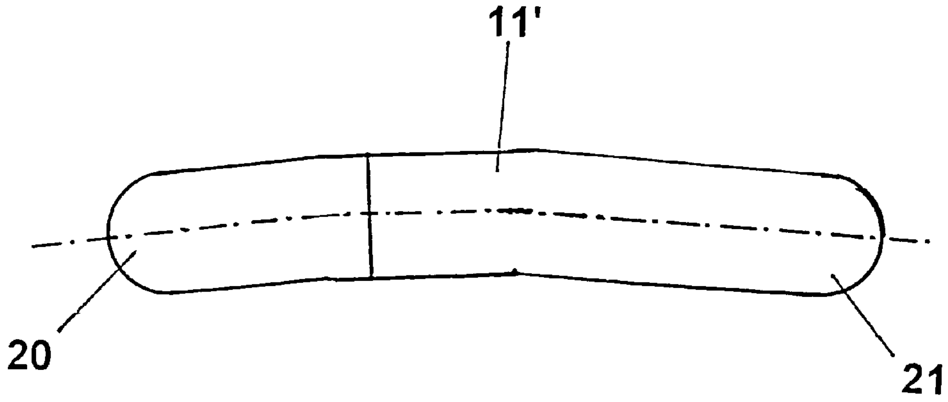
FIG. 4 shows a side view of a medical implant with a housing in accordance with another embodiment of the present invention including a plurality of bends in one plane.
Figure 5:
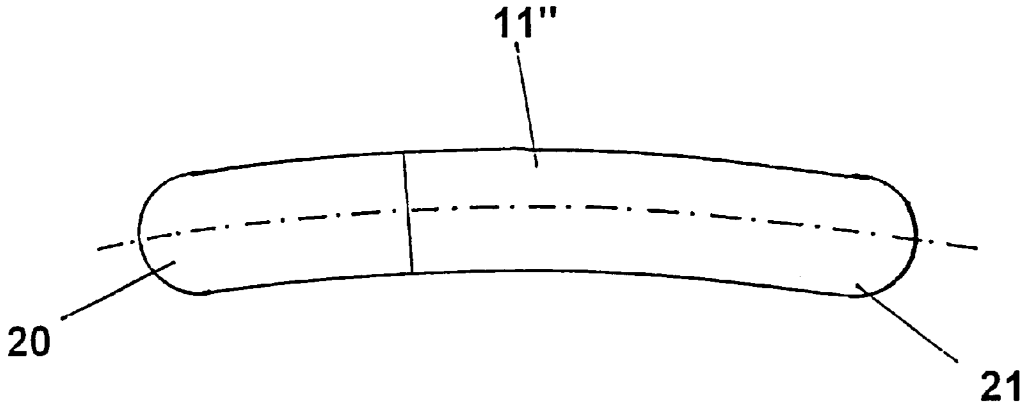
FIG. 5 shows a side view of a medical implant with a housing in accordance with another embodiment of the present invention wherein the housing is curved in one plane.

FIG. 4 shows another embodiment of present invention including a double-bent housing 11'. FIG. 5 also shows another embodiment of the present invention including a curved housing 11". Both of these housings 11' and 11" are designed such that a tangential line extending from a bottom portion 19 on one housing end 20 forms an angle $\alpha$ in the range from 5° to 25° with a tangent extending from the other housing end 21.

The present invention can be applied to relatively wide housings by providing one or more bends or a curvature in the longitudinal direction of the implant housing. Furthermore, in such applications, the present invention is especially advantageous if one or more bends or a curvature is provided not only in the longitudinal direction, but also in the transverse direction of the implant housing. Extensive clinical tests have shown that this implant housing design minimized any protrusion of the implant housing from the artificial bone bed in the mastoid of the skull while increasing the volumetric capacity of the housing when compared to conventional housing designs.

The implant housing materials can be chosen in the conventional manner considering the design and application requirements noted previously. The preferred metallic materials that may be used in the present invention include titanium, titanium alloys, niobium, niobium alloys, cobalt-chromium alloys and stainless steels which are biocompatible and corrosion-proof Suitable ceramic materials include aluminum oxide and boron nitride among others.

While various embodiments in accordance with the present invention have been shown and described, it is understood that the invention is not limited thereto, and may be changed, modified and further applied by those skilled in the art. Therefore, this invention is not limited to the details shown and described previously but also includes all such changes and modifications which are encompassed by the claims.

We claim:

1. Medical implant for implantation in a bone bed in the skull comprising a hermetically sealed housing for accommodating electronic components, said housing having at least one surface including at least one bend, wherein said at least one surface comprises a bottom surface of the housing which is shaped such that a line tangential to one end portion of said bottom surface forms an angle of between 5° and 25° with a line tangential to an opposite end portion of said bottom surface; and wherein said bend is located between said end portions.

2. Medical implant of claim 1, wherein the lines intersect to form said angle in a middle third region of said housing.

3. Medical implant of claim 1, wherein the lines intersect to form said angle between in a middle region of said housing.

4. Medical implant of claim 1, wherein said housing includes a plurality of bends in at least one plane.

5. Medical implant of claim 1, wherein said housing is curved in at least one plane.

6. Medical implant of claim 1, wherein the electronic components are parts of an active hearing aid for stimulation of the middle or inner ear; and wherein said housing is made of a biocompatible material for enabling implantation thereof.

7. Medical implant of claim 1, wherein said angle is between 7° and 15°.

8. Medical implant of claim 1, wherein said angle is substantially 10°.

9. Medical implant of claim 1, wherein a largest dimension of said housing is between 30 mm and 55 mm and said at least one bend runs in a direction perpendicular to said largest dimension.

10. Medical implant of claim 9, wherein said largest dimension of said housing is between 38 mm and 50 mm.

11. Medical implant of claim 10, wherein said largest dimension of said housing is substantially 43 mm.

12. Medical implant of claim 1, wherein a smallest dimension of said housing is between 4 mm and 8 mm.

13. Medical implant of claim 12, wherein said smallest dimension of said housing is substantially 7 mm.

14. Medical implant of claim 1, wherein said housing is rigid.

15. Medical implant of claim 1, wherein said housing is made from a ceramic material.

16. Medical implant of claim 1, wherein said housing comprises a ceramic housing portion joined to a metal housing portion.

17. Medical implant of claim 16, wherein said at least one bend is substantially positioned where said ceramic housing portion is joined to said metal housing portion.

18. Medical implant of claim 1, wherein said housing contains an electronic implant unit and an implantable component of a power supply unit.

19. Medical implant of claim 1, wherein said housing contains at least one of a transmitting coil and a receiving coil.

20. Medical implant of claim 1, wherein said housing contains a single coil both for receiving energy and for data transmission.

21. Medical implant of claim 1, wherein said housing contains a coil for receiving energy for recharging an energy storage device of the implant.

22. Medical implant of claim 16, wherein said ceramic housing portion contains at least one of a transmitting coil and a receiving coil.

23. Medical implant of claim 1, wherein said implant is a component in a hearing aid which is totally implantable.

24. Medical implant of claim 1, wherein said implant is a component in a hearing aid which is partially implantable.

25. Medical implant of claim 23 or 24, wherein said hearing aid is an active hearing aid which stimulates portions of the inner ear.

* * * * *